United States Patent [19]

Vance et al.

[11] Patent Number: 5,527,298
[45] Date of Patent: Jun. 18, 1996

[54] TRACKING GUIDEWIRE

[75] Inventors: Jeffrey D. Vance, Hugo; Rick L. Shockey, Coon Rapids, both of Minn.

[73] Assignee: Schneider (USA) Inc., Plymouth, Minn.

[21] Appl. No.: 989,686

[22] Filed: Dec. 14, 1992

(Under 37 CFR 1.47)

Related U.S. Application Data

[63] Continuation-in-part of Ser. No. 851,224, Mar. 12, 1992, abandoned, which is a continuation of Ser. No. 535,932, Jun. 11, 1990, abandoned.

[51] Int. Cl.⁶ ............................................... A61M 25/00
[52] U.S. Cl. .................. 604/280; 604/164; 604/170; 604/264; 604/282; 128/772; 606/191
[58] Field of Search ....................... 128/656–658, 128/772; 606/191, 197, 198, 199; 604/164–166, 170, 264, 267, 274, 282, 280

[56] References Cited

U.S. PATENT DOCUMENTS

| | | | |
|---|---|---|---|
| 1,327,786 | 1/1920 | Stephan | 606/197 |
| 1,665,564 | 4/1928 | Reitz | 604/104 |
| 1,920,006 | 7/1933 | Dozier et al. . | |
| 3,196,876 | 7/1965 | Miller . | |
| 3,572,333 | 3/1971 | Hubert | 604/170 |
| 3,999,551 | 12/1976 | Spitz et al. . | |
| 4,013,079 | 3/1977 | Lindemann et al. . | |
| 4,388,076 | 6/1983 | Waters . | |
| 4,538,622 | 9/1985 | Samson et al. . | |
| 4,676,249 | 6/1987 | Arenas et al. . | |
| 4,793,363 | 12/1988 | Ausherman et al. . | |
| 4,795,458 | 1/1989 | Regan . | |
| 4,798,591 | 1/1989 | Okada | 614/164 |
| 4,834,709 | 5/1989 | Banning et al. | 604/170 |
| 4,854,325 | 8/1989 | Stevens | 128/772 |
| 4,854,330 | 8/1989 | Evans, III et al. . | |
| 4,873,983 | 10/1989 | Winters . | |
| 4,925,445 | 5/1990 | Sakamoto et al. . | |
| 5,127,917 | 7/1992 | Niederhauser et al. . | |
| 5,154,705 | 10/1992 | Fleischhacker et al. | 604/282 |

FOREIGN PATENT DOCUMENTS

| | | |
|---|---|---|
| 0242985 | 10/1987 | European Pat. Off. . |
| 0452631 | 10/1991 | European Pat. Off. ............... 606/191 |
| 9119528 | 12/1991 | WIPO . |

OTHER PUBLICATIONS

Trimedyne Laserprobe Brochure, 1988.

Primary Examiner—C. Fred Rosenbaum
Assistant Examiner—Ronald K. Stright, Jr.
Attorney, Agent, or Firm—Peter C. Richardson; Lawrence C. Akers; Philip C. Strassburger

[57] ABSTRACT

A guidewire for placement within a blood vessel for penetrating an occlusion therein. The guidewire comprises a length of flexible wire having a lumen extending therethrough. The distal end of the guidewire is generally arcuate and has a diameter greater than that of the wire immediately proximal thereto. A flexible stylet substantially the same length as the flexible wire may be disposed within the lumen of the wire. In operation, the arcuate distal end of the guidewire is positioned in the blood vessel against an occlusion, and a dottering action is thereafter provided whereby the arcuate distal end of the guidewire repeatedly impinges on the occlusion until penetration of the occlusion occurs.

17 Claims, 2 Drawing Sheets

TRACKING GUIDEWIRE

This is a continuation-in-part of application Ser. No. 7/851,224 filed Mar. 12, 1992 now abandoned which is a continuation of application Ser. No. 07/535,932 filed Jun. 11, 1990 now abandoned.

BACKGROUND OF THE INVENTION

This invention relates generally to a tracking guidewire, and in particular to an occlusion-penetrable guidewire having a lumen throughout its entire length into which a stylet can be inserted. Preferably the distal end portion of the guidewire is arcuate and has a diameter greater than that of the immediately proximal wire.

Vessel entry for treatment of certain untoward health conditions is a common practice. Such entry can include insertion into a blood vessel of a guidewire whose distal end is expected to reach a certain site within the body and have utility thereafter as required. Many times, however, a blood vessel may be completely or almost completely occluded, thereby rendering it substantially impossible to advance a guidewire there beyond to a designated site without first employing a separate procedure to remove the occlusion.

It is therefore a primary object of the present invention to provide a guidewire having a lumen running its entire length and a distal end portion capable of penetrating a vascular occlusion. Another object of the present invention is to provide such a guidewire wherein the tip of the distal end portion is arcuate and the diameter of the distal end portion is greater than that of the immediately proximal wire. Yet another object of the present invention is to provide a guidewire assembly wherein a stylet can be removably inserted into the length of the guidewire lumen to thereby enhance guidewire structure. These and other objects will become apparent throughout the description which now follows.

SUMMARY OF THE INVENTION

The present invention is a guidewire for placement within a blood vessel for penetrating an occlusion in the vessel. The guidewire comprises a length of flexible wire having a concentric lumen running its entire length. At its proximal end, the wire has an opening to the lumen. At its distal end, the wire has an arcuate tip with a diameter greater than the diameter of the wire immediately proximal thereto.

In addition, the guidewire may include a flexible stylet substantially the same length as the guidewire that is removably inserted into the lumen of the guidewire. Such stylet placement provides a greater stiffness and structural integrity to the guidewire.

Finally a method of penetrating an occlusion in a blood vessel is disclosed. The method comprises inserting the guidewire into an occluded blood vessel. Initially, the stylet is positioned in the lumen of the guidewire so that it extends into the arcuate tip portion. When the guidewire contacts the lesion site, the stylet is removed from at least the distal end of the guidewire. This allows the arcuate tip to center itself at the proximal portion of the lesion site. Thereafter, the stylet is fully inserted into the arcuate tip of the guidewire. A dottering action, i.e. a back and forth movement to impinge the arcuate tip against the lesion, is provided to the guidewire. This dottering action is carried out for a sufficient period of time whereby the repeated impingement upon the occlusion results in penetration thereof. After the distal end of the guidewire has passed through the occlusion, the stylet can be withdrawn and a contrast medium can be injected into the lumen to confirm guidewire positioning within the vessel.

BRIEF DESCRIPTION OF DRAWINGS

Presently preferred embodiments of the invention are illustrated in the accompanying drawings in which like reference numerals refer to like parts throughout and in which.

DETAILED DESCRIPTION OF PREFERRED EMBODIMENTS

Figure 1:
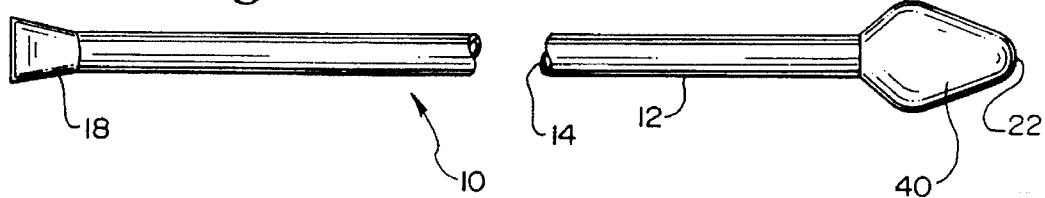
FIG. 1 is a side elevation view of one embodiment of the guidewire of this invention without a stylet inserted therein.

The guidewire 10 of this invention comprises a length of flexible wire 12 having a lumen 14 running the entire length of wire 12. A proximal end hub 18 opens to lumen 14. The distal end 20 of wire 12 has an arcuate tip 22 with a diameter greater than the diameter of wire 12 immediately proximal to distal end 20. Guidewire 10 can be conventionally constructed of metal core, and is preferably constructed of metal coils.

Figure 2:
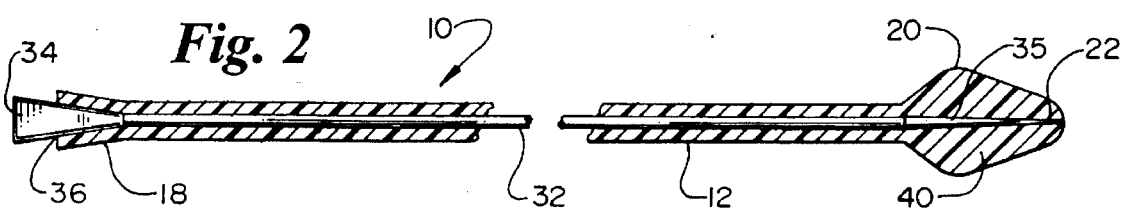
FIG. 2 is a side elevation view partially in section of one embodiment of the guidewire of this invention with the stylet inserted therein.
Figure 3:
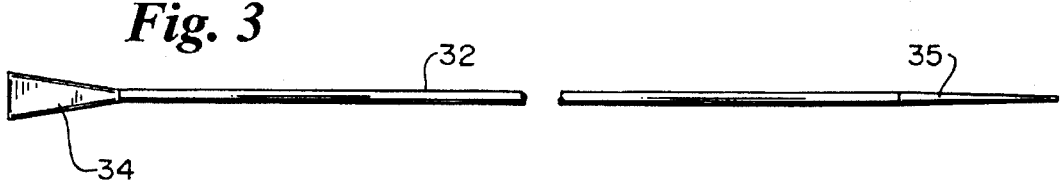
FIG. 3 is a side elevation view of a stylet.
Figure 6:
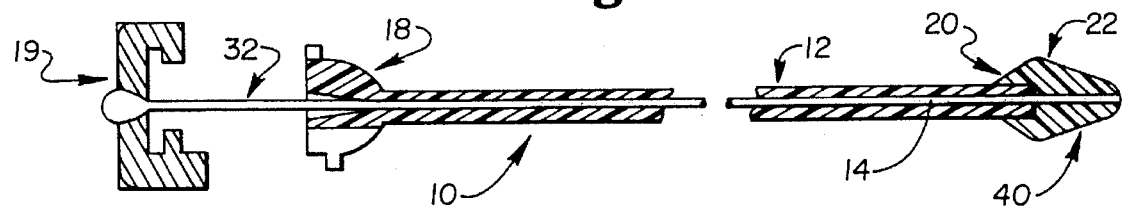
FIG. 6 is a side elevation cross-sectional view of a fourth embodiment of the guidewire of this invention with a stylet partially inserted therein.
Figure 7:
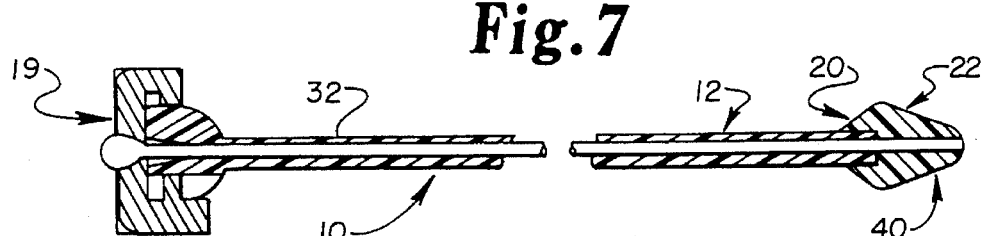
FIG. 7 is a side elevation cross-sectional view of the fourth embodiment of the guidewire of this invention with a stylet fully inserted therein.
Figure 8:
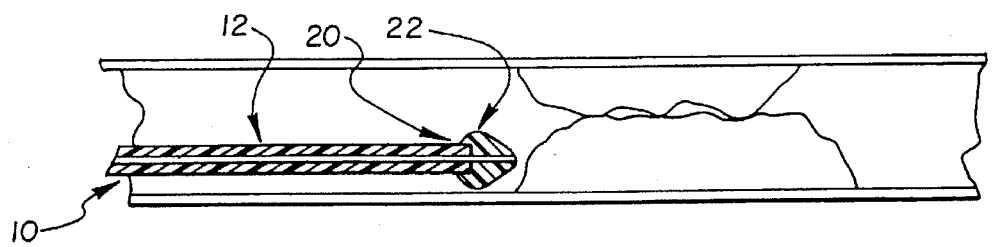
FIGS. 8, 9 and 10 are side elevation views of a partially occluded blood vessel with the guidewire of this invention being used to effect penetration through the occlusion.
Figure 9:
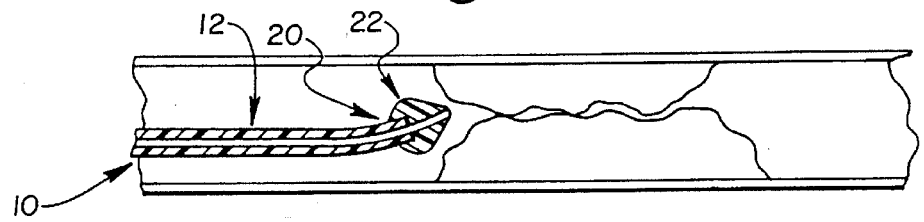
Figure 10:
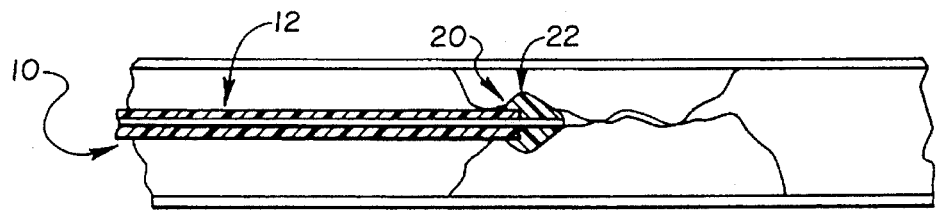

A flexible stylet 32, as shown in FIG. 3, may be disposed within lumen 14 of wire 12. Stylet 32 is substantially the same length as wire 12 so that stylet 32 preferably does not extend beyond distal end 20 of arcuate tip 22. The distal end 35 of stylet 32 may be tapered as shown in FIGS. 2 and 3. In addition, stylet 32 has a proximal end member 34 whose shape is complementary to the interior wall 36 of hub 18. Preferably a locking means 19, such as conventional Luer locking threads, is used to securely maintain stylet 32 within lumen 14. Luer locking threads also provide releasability for withdrawal of stylet 32 as required. See FIGS. 6 and 7. Stylet 32 can be constructed of metal or polymer core, and is preferably constructed of metal.

Figure 4:
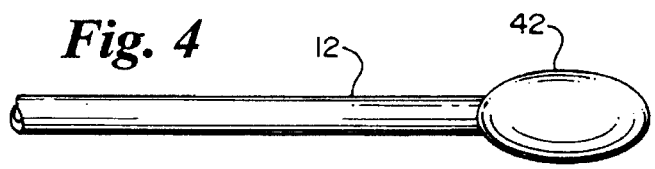
FIG. 4 is a partial side elevation view of a second embodiment of a distal end of the guidewire of this invention.
Figure 5:
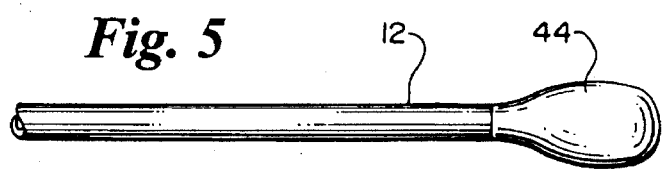
FIG. 5 is a partial side elevation view of a third embodiment of a distal end of the guidewire of this invention.

As earlier noted, distal end 20 of wire 12 has an arcuate tip 22 and has a diameter which is greater than that of wire 12 immediately proximal thereto. Three non-limiting examples of preferred shapes of distal end 20 are illustrated in the Figures. Specifically, FIGS. 1, 2 and 6–10 show an arrowhead shape 40; FIG. 4 shows an elliptical shape 42; and FIG. 5 illustrates a tear-drop shape 44. It is to be understood, of course, that shapes other than those illustrated can be employed as long as an arcuate tip is provided to thereby enhance physical intrusion of an occlusion. The various shapes of the respective distal ends are attained in the manufacturing process which can include EDM machining and grinding.

In operation, guidewire 10, and in particular arcuate tip 22 and distal end 20, functions to penetrate an occlusion in a blood vessel. The user inserts guidewire 10 with stylet 32 fully inserted into distal end 20 into a blood vessel and positions arcuate tip 22 against the proximal wall of an occlusion. See FIG. 8. Once placed, stylet 32 is withdrawn from distal end 20. This gives guidewire 10 more flexibility and allows the user to easily center distal end 20 against the occlusion. See FIG. 9. At this point, stylet 32 can be fully inserted into distal end 20. See FIG. 10. Guidewire 10 is then subjected to a dottering action, i.e. a repeated back and forth movement, by the user to effectuate a repeated impinging action upon the occlusion by arcuate tip 22 and distal end 20. This dottering action is continued for a period of time sufficient to penetrate the entire length of the occlusion and thereby permit continued travel of guidewire 10 itself or of other apparatus through the occlusion. Once distal end 20 of guidewire 10 is through the occlusion, stylet 32 can be removed from lumen 14 and a contrast medium can be injected into lumen 14 to thereby confirm the true position of distal end 20. Of course, guidewire 10 may be used to cross an occlusion without stylet 32 located in lumen 14.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A guidewire for placement within a blood vessel for penetrating an occlusion therein comprising:
   (a) a flexible metal wire having a proximal end and a distal end and a lumen extending through the wire wherein the distal end of the wire has an arcuate tip having a diameter greater than the diameter of the wire immediately proximal thereto; and
   (b) a flexible, tapered, stylet having a proximal end and a distal end, the stylet configured for insertion into the flexible wire lumen such that the distal end of the stylet can retractably extend into the tip of the flexible wire; the stylet providing greater stiffness to the guidewire along the length of the stylet's extension.

2. The guidewire of claim 1 further comprising:
   (c) locking means for releasably securing the stylet to the wire.

3. The guidewire of claim 1 wherein the locking means is adapted to releasably secure the proximal end of the stylet to the proximal end of the wire.

4. The guidewire of claim 1 wherein the locking means comprises locking threads.

5. The guidewire of claim 1 wherein the wire lumen opens to a hub on the proximal end of the wire and the stylet has a proximal end member having a shape which is complimentary to a shape of the wire hub.

6. A guidewire for placement within a blood vessel for penetrating an occlusion therein comprising:
   (a) a flexible metal wire having a proximal end and a distal end and a lumen extending through the wire wherein the distal end of the wire has an arcuate tip having a diameter greater than the diameter of the wire immediately proximal thereto;
   (b) a flexible stylet having a proximal end and a distal end, the stylet configured for insertion into the flexible wire lumen such that the distal end of the stylet can retractably extend into the tip of the flexible wire; the stylet providing greater stiffness to the guidewire along the length of the stylet's extension; and
   (c) locking means for releasably securing the stylet to the wire.

7. The guidewire of claim 6 wherein the locking means is adapted to releasably secure the proximal end of the stylet to the proximal end of the wire.

8. The guidewire of claim 6 wherein the locking means comprises locking threads.

9. The guidewire of claim 6 wherein the stylet is tapered.

10. The guidewire of claim 6 wherein the wire lumen opens to a hub on the proximal end of the wire and the stylet has a proximal end member having a shape which is complimentary to a shape of the wire hub.

11. A guidewire for placement within a blood vessel for penetrating an occlusion therein comprising:
   (a) a flexible metal wire having a proximal end and a distal end and a lumen extending through the wire wherein the distal end of the wire has an arcuate tip having a diameter greater than the diameter of the wire immediately proximal thereto; and
   (b) a flexible stylet having a proximal end and a distal end, the stylet configured for insertion into the flexible wire lumen such that the distal end of the stylet can retractably extend into the tip of the flexible wire; the stylet providing greater stiffness to the guidewire along the length of the stylet's extension;
   wherein the wire lumen opens to a hub on the proximal end of the wire and the stylet has a proximal end member having a shape which is complimentary to a shape of the wire hub.

12. The guidewire of claim 11 further comprising:
   (c) locking means for releasably securing the stylet to the wire.

13. The guidewire of claim 11 wherein the locking means is adapted to releasably secure the proximal end of the stylet to the proximal end of the wire.

14. The guidewire of claim 11 wherein the locking means comprises locking threads.

15. The guidewire of claim 11 wherein the stylet is tapered.

16. A method of penetrating an occlusion in a blood vessel, the method comprising:
   (a) providing a guidewire comprising:
      (i) a flexible wire having a proximal end and a distal end and a lumen extending through the wire wherein the distal end of the wire has an arcuate tip having a diameter greater than the diameter of the wire immediately proximal thereto; and
      (ii) a flexible stylet having a proximal end and a distal end, the stylet configured for insertion into the flexible wire lumen such that the distal end of the stylet can retractably extend into the tip of the flexible wire;
   (b) inserting the stylet into the flexible wire and pushing the stylet until its distal end is in the tip of the flexible wire;
   (c) inserting the guidewire into the blood vessel and positioning the distal end of the wire against the occlusion;
   (d) retracting the stylet so that the distal end of the stylet moves toward the proximal end of the wire;
   (e) centering the distal end of the wire at the occlusion;
   (f) pushing the stylet so that the distal end of the stylet moves toward the distal end of the wire; and (g) pushing the guidewire so that the tip of the guidewire enters the occlusion.

17. The method of claim 16 further comprising:

(h) providing a dottering action to the guidewire for a period of time whereby the distal end of the wire repeatedly impinges upon the occlusion.

* * * * *